(12) United States Patent
Brady

(10) Patent No.: US 7,563,756 B2
(45) Date of Patent: Jul. 21, 2009

(54) SCENTED TABLET FOR TOILET AND METHOD FOR SCENTING RESTROOM EFFLUENT

(76) Inventor: Brandi Brady, 4127 Arlington Dr., Richton Park, IL (US) 60471

(*) Notice: Subject to any disclaimer, the term of this patent is extended or adjusted under 35 U.S.C. 154(b) by 779 days.

(21) Appl. No.: 10/925,087

(22) Filed: Aug. 24, 2004

(65) Prior Publication Data
US 2005/0049154 A1    Mar. 3, 2005

Related U.S. Application Data

(60) Provisional application No. 60/497,975, filed on Aug. 27, 2003.

(51) Int. Cl.
C11D 17/00    (2006.01)
A61L 9/00    (2006.01)
A61L 11/00    (2006.01)

(52) U.S. Cl. ............... 510/191; 424/76.2; 424/76.7; 422/5

(58) Field of Classification Search .......... 510/191, 510/192, 193; 424/76.2, 76.7; 422/5
See application file for complete search history.

(56) References Cited

U.S. PATENT DOCUMENTS

| | | | | |
|---|---|---|---|---|
| 3,242,093 A * | 3/1966 | Compton | ............ | 510/245 |
| 3,365,315 A | 1/1968 | Beck | | |
| 3,867,101 A * | 2/1975 | Herring | ............ | 422/119 |
| 3,985,298 A | 10/1976 | Nichols | ............ | 239/54 |
| 4,155,897 A | 5/1979 | Schlüsener | ............ | 260/40 R |
| 4,578,207 A | 3/1986 | Holdt | ............ | 252/134 |
| 4,852,201 A | 8/1989 | Wundrock | ............ | 15/145 |
| 5,336,665 A | 8/1994 | Garner-Gray | ............ | 512/4 |
| 5,543,439 A | 8/1996 | McDermott | ............ | 523/102 |
| 5,725,869 A | 3/1998 | Lo | ............ | 424/408 |
| 5,759,574 A | 6/1998 | Bothe | ............ | 424/464 |
| 5,824,345 A | 10/1998 | Milstein | ............ | 424/489 |
| 5,849,055 A | 12/1998 | Arai | ............ | 65/17.3 |
| 5,871,722 A | 2/1999 | Nacht | ............ | 424/78.03 |
| 5,997,901 A | 12/1999 | Mills | ............ | 424/464 |
| 6,124,251 A | 9/2000 | Rader | ............ | 510/191 |
| 6,235,127 B1 | 5/2001 | Rader | ............ | 134/42 |
| 6,440,915 B2 | 8/2002 | Rader | ............ | 510/191 |
| 6,451,754 B1 * | 9/2002 | Rowland et al. | ............ | 510/446 |
| 6,486,111 B1 * | 11/2002 | Zabarylo et al. | ............ | 510/314 |
| 6,589,924 B2 * | 7/2003 | Schmidt et al. | ............ | 510/191 |
| 6,677,296 B2 * | 1/2004 | Bonsall | ............ | 510/446 |
| 6,703,012 B1 | 3/2004 | White | ............ | 424/76.7 |
| 6,713,441 B1 * | 3/2004 | DeSenna et al. | ............ | 510/191 |
| 6,730,647 B2 | 5/2004 | Wäschenbach | ............ | 510/224 |
| 6,747,000 B2 | 6/2004 | Pearce | ............ | 510/446 |
| 6,769,271 B2 | 8/2004 | Mosbaugh | ............ | 65/17.3 |

(Continued)

*Primary Examiner*—Lorna M Douyon
(74) *Attorney, Agent, or Firm*—William L. Muckelroy; Art Lessler; Gary Lipson

(57) ABSTRACT

A fragrance formulation that uses effervescing agents to emit a fragrance from a non-splashing cone-shaped delivery tablet. The cone shaped tablet provides a short timed release and delivery of fragrance agents after immersion in a toilet bowl. The method of use includes the step of dropping the cone shaped tablet tip first into the water in the toilet bowl. The tablet composition comprises a pre-glass agglomeration powder with absorbed fragrance oils bound to an effervescing agent such as sodium bicarbonate in a binder of boric acid, citric acid, and water. Use of the tablet effectively fills a powder room with a pleasant masking scent over a short time period, e.g. 30 minutes to 1 hour.

5 Claims, 1 Drawing Sheet

U.S. PATENT DOCUMENTS 6,770,616 B1 8/2004 McGowan .................. 510/446
2002/0061831 A1* 5/2002 Kaziska et al. .............. 510/446
2002/0187119 A1* 12/2002 Greer et al. ................ 424/76.2

* cited by examiner

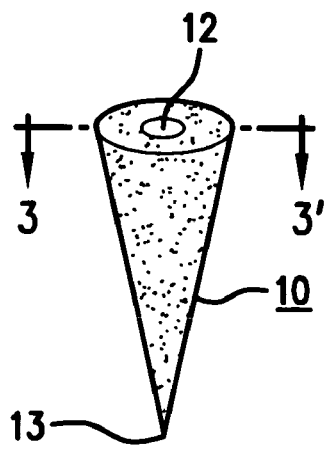
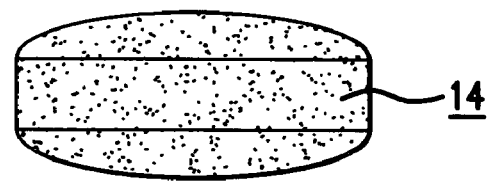
FIG.1
FIG.2 PRIOR ART
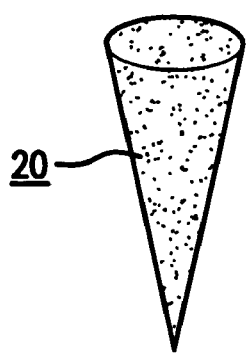
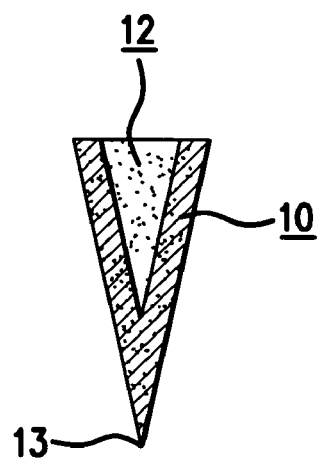
FIG.4
FIG.3

SCENTED TABLET FOR TOILET AND METHOD FOR SCENTING RESTROOM EFFLUENT

CROSS REFERENCE TO RELATED APPLICATIONS

Applicant claims the benefit of a priority date, namely, the filing date of U.S. provisional application No. 60/497,975 filed on Aug. 27, 2003 and entitled "Tablet formulation and related method for effervescing fragrance from conventional toilet bowl".

BACKGROUND OF THE INVENTION

1. Field of the Invention

This invention relates to formulations for solid tablets containing agents that are emitted by effervescing and dissolving actions when placed in water, and in particular to a composite in-bowl toilet tablet for deposit into a toilet bowl and for providing the quick release of a scent over a short period of time and a reduced splash structure for improving the method for depositing such a tablet composite such that it does not splash out toilet water.

The present invention relates to a structure and method for making and using fragrance delivery systems. In particular, the invention relates to a method of using a pre-glass agglomeration that adsorbs fragrance producing oils and volatiles, and quickly releases the fragrance innate to the oils and volatiles over a short period of time when dropped in toilet bowl water by incorporating an effervescing agent and action.

2. Prior Art

Most fragrance delivery systems that utilize microspheres are manufactured out of acrylates or nonsiliceous polymers. There are no fragrance delivery systems that utilize soda lime borosilicate microspheres fused together naturally without additives. Most fragrance systems have a short life span and this is usually considered undesirable. The current invention utilizes this shortfall to meet a specific feminine hygiene related need and create a new product. Virtually all-available fragrance systems complain that they only last a short time and consider this a drawback whereas the current application recognizes a utility and need to have a very intense smell initially with a reasonably pleasant odor that fades fairly fast.

Microspheres have been used in the past for a variety of purposes. The most common uses pertain to holders for chemicals in compositions such as holding fragrance for laundry detergent. In other words, the microspheres contain a chemical and are mixed with other compounds to form a heterogeneous composition where the microspheres will release the chemicals either gradually or all at once in response to a stimulus such as a change in ionic character, heat or other stimulus.

The material, shape, and utility combined by this invention are unique. The combination of sodium bicarbonate, citric acid, and the pre-glass agglomeration created by this invention was unknown in the past. The pre-glass agglomerations used as a fragrance vehicle are not discrete spheres but rather modified soda-lime borosilicate sphere clusters, wherein thousands of microspheres become molecularly fused together via microcrystalline-like structures on the sphere surfaces. Therefore, this invention provides a method of making a microsphere.

U.S. Pat. No. 3,365,315 issued to Beck, et al. on Jan. 23, 1968, discloses glass bubbles made from glass cullet particles by heating. This amorphous solid contains $SiO_2$ (60-80%), $Na_2O$ (5-26%), CaO (5-25%), $K_2O/Li_2O$ (5-16%), and $Na_2O/K_2O/Li_2O$ (5-16%) plus some other oxides. The temperature range utilized for bubble formation is between 1050° C. and 1300° C. The resultant amorphous solid can be utilized as an ingredient in molded parts designed for use in high pressure environments. The methods utilized to make the glass bubbles taught by Beck, as well as the glass bubbles themselves, are very different from the powdered rock of the present invention.

U.S. Pat. No. 3,985,298 issued to Nichols on Oct. 12, 1976, discusses controlled release materials, and method of using, that can be incorporated into a chemical delivery system. The materials utilized by Nichols are polymer-liquid composite materials which may contain 99% or more of the liquid. These controlled release materials can be incorporated into aerosol propellants, food products, chewing gum, pharmaceutical compounds, agricultural products, or cosmetic preparations. The desired functions of the release materials include scenting. However, the materials and objectives utilized by Nichols are different from the present invention.

U.S. Pat. No. 4,155,897 issued to Schlusener on May 22, 1979, discloses compositions exhibiting controlled release of an active substance. The compositions of Schlusener comprise an unsaturated polyester resin, an active substance, hollow microspheres of an organic material, and an inorganic material. The hollow microspheres can be made of glass and are mixed with an unsaturated polyester resin to make a molded solid or semisolid substance. An active ingredient, such as volatile oils, is added to the substance. The composition taught by Schlusener is an adequate substitute for the amorphous rock powder of the present invention. Schlusener is suitable since there is a relatively high initial gas release rate. However, without the effervescing feature the rate is not suitable for the utility of the present invention.

U.S. Pat. No. 5,336,665 issued to Garner-Gray, et al. on Aug. 9, 1994, discloses a hydrophobic porous inorganic carrier particle having a perfume absorbed into the particle. A detergent composition containing the carrier particle and a method for manufacturing the same are disclosed. The inorganic carriers used in Garner-Gray include aluminosilicates such as certain zeolites, clays, aluminas and silicas, all of which are chemically treated or naturally hydrophobic. These porous, inorganic carrier particles are not suitable for the current invention since although they release odor over a short or quick period of time, they are hydrophobic and will not adsorb water or alcohols.

U.S. Pat. No. 5,725,869 issued to Lo on Mar. 10, 1998, describes microsphere reservoirs for controlled release applications. The microspheres, optionally containing an ingredient to be dispensed through controlled release, is prepared by solvent evaporation of an oil-in-water emulsion formed from an organic solvent containing a polymer and a plasticizer and an aqueous solution containing one or more emulsifying agents. The microcapsules formed are porous and spongy in structure as opposed to hollow. These microspheres have a relatively high load rate and a low dispersion rate. They are useful for the current invention as a carrier for fragrances when combined with an effervescing agent. The invention of Lo is not designed or recognized to be a room deodorizer.

U.S. Pat. No. 5,824,345 issued to Milstein on Oct. 20, 1998, discloses compositions useful in the delivery of fragrances. A method for preparing the compositions is disclosed: the active agent is mixed with the proteinoid of hydrolyzed vegetable protein solution and the proteinoid of modified hydrolyzed vegetable protein is precipitated out of the solution, thereby forming a microsphere containing the active agent. The product formed by the method in Milstein differs from Mosbaugh pre-glass agglomerate powder used in the present invention in that the present invention adsorbs any liquid, oil or alcohol, while Milstein requires the microspheres to be made concurrent with placing the agent therein which is a handicap.

U.S. Pat. No. 5,849,055 issued to Arai, et al. on Dec. 15, 1998, discloses a process for making inorganic microspheres which comprises pulverizing a material by wet pulverization to obtain a slurry of a pulverized powder material, spraying the slurry to form liquid droplets, and heating the liquid droplets to fuse or sinter the powder material to obtain inorganic microspheres. These microspheres are discrete individual microbeads and can be utilized to make the composite for use in the manner of the present invention. The novel invention recognizes that the microspheres of Arai can be used as an effective scent carrying powder ingredient and for effervescing scent delivery when combined with sodium bicarbonate.

U.S. Pat. No. 5,871,722 issued to Nacht, et al. on Feb. 16, 1999, shows ionic beads useful for controlled release and adsorption. Active ingredients are released from the ionic polymer beads over an extended period of time contrary to the novel utility of the current invention. These beads would not be useful for room deodorants or absorption of oils.

It is well accepted in the feminine toiletries industry that young women feel insecure during the period of the month when in a restroom and after leaving a restroom following changing sanitary napkins or tampons and addressing related sanitary needs. The novel invention is a new product and method of use for it designed to make women feel more secure after leaving the restroom by providing a single use tablet therein. Until McDermott et al, the advantages of polyvinyl alcohol and partially hydrolyzed polyvinyl acetate had not previously been obtained in toilet block applications, and other additives had to be included in the toilet block compositions in order to provide the desired aroma control release and solubility/dispersibility characteristics.

Although the water-soluble compositions of McDermott et al have excellent aroma and solubility properties, the foaming performance and prior art shapes of these compositions if dropped into a toilet bowl do not achieve the objectives of the novel invention. U.S. Pat. No. 5,997,901, which issued to Mills on Dec. 7, 1999 details a method of manufacturing scented molded products, designed to effervesce over an extended time as a bath tablet or an air freshener. However, the tablet of Mills, if dropped into a toilet bowl in the usual pill shaped form there is considerable undesirable splashing and insufficient fragrance is issued to scent a bathroom or powder room because of the over reliance on the effervescing agent as weight percentage of the tablet.

Conventionally, effervescent bath tablets are made by molding components together under pressure in a block or pill shaped form. Typically, one of the components is a volatile ingredient, for example, isopropyl alcohol or products such as propylene glycol or oils such as canola or almond. These are used as a binding agent and impede rapid dissolution of the tablets when placed in water at room temperature and thereby impede the rate of delivery of fragrance from room temperature toilet bowl water.

SUMMARY OF THE INVENTION

According to the present invention, there is provided a solid composition of matter which comprises a water-soluble, or water-dispersible composite, a compatible fragrance, either as a blend of fragrance with polymer or separately mixed, and one or more binders.

The composition of matter of the present invention has, unexpectedly and advantageously, excellent foaming properties, better than the compositions of U.S. Pat. No. 5,543,439 and conventional toilet elements, as well as improved aroma behavior, short-time fragrance emission performance and solubility/dispersibility characteristics, which are comparable, and at least as good as, the aroma properties, short term performance and solubility/dispersibility characteristics of the compositions of U.S. Pat. No. 5,997,901 issued to Mills in 1999. The novel composition of the present invention is shaped in a novel projectile-like or cone shape for reducing splashing when dropped into a toilet bowl containing water. The cone shaped composition is further hollowed out to shift its center of gravity towards the tip to further insure nose or tip first entry into the water.

OBJECT OF THE INVENTION

The primordial objective is to create a non-splashing product such as a purse-sized tablet weighing from 40 to 200 grams to drop into a toilet bowl and for an immediate pleasurable fragrance to be released and to perfume a small restroom.

The secondary objective was to create a novel tablet that releases an immediate pleasurable fragrance lasting about 30 minutes to 1 hour. Moreover, a water-activated, water dissolving, scent-releasing tablet that did not splash water from the toilet bowl when dropped therein was designed.

It is therefore an object of the present invention to provide a water-soluble, water-dispersible composition having improved foaming performance, without compromising excellent aroma behavior, and solubility and dispersibility characteristics desirable for a new relatively instantaneous toilet scenting application whereby the nature and shape of the composition allows it to be dropped into a toilet with minimized splashing.

The novel invention will be fully understood in all of its aspects from the drawings and the specification that follows, to wit:

BRIEF DESCRIPTION OF THE DRAWING

FIG. 1 is a perspective view of a first embodiment of the novel invention.

FIG. 2 is a view of the prior art.

FIG. 3 is a perspective view of a second embodiment of the novel invention.

FIG. 4 is a cross-sectional view of the first embodiment shown along the plane 3-3'.

DETAILED DESCRIPTION OF THE PREFERRED EMBODIMENT

The present invention is partly based on recognition of the fact that it is preferable to avoid splashing when dropping a fragrancing tablet into a toilet bowl for the objective specified here, especially when sticky substances such as oils are used to effect a binding together of the components of the tablets by means of a chemical binding process. The inventor has discovered that by utilizing some pressure and by forming the tablet into a projectile-like shape splashing is reduced considerably when the tablet is dropped into the toilet bowl. Thus, the novel invention is partly based on employing a method of use wherein a novel projectile shaped tablet is dropped into the toilet water with the pointed end first.

Secondly, it is preferable to use an admixture for the tablets wherein a primary citric acid fragrance delivery system and a secondary pre-glass agglomerate powder fragrance delivery system are employed. The secondary system is powdered fused microspheres incorporating the fragrance interspersed with an effervescing agent. The primary but weaker delivery system is the fragrance delivered from the citric acid. Both are combined as a composition as further described herein.

The novel composition is preferably made into a novel hydrodynamically efficient shape, a cone 10 for example, with a cone-shaped plenum 12 in the center thereof as shown in FIG. 1. The composition is formed as the cone 10: (a) to minimize splashing; (b) to immediately emit a fragrance; and, (c) to immediately effervesce when dropped into the water in a toilet bowl (not shown). As described, somewhat similar compositions are known in the prior art but shaped like a conventional tablet 14 such as shown in FIG. 2 (prior art). Regardless of distance to the water surface, prior art shaped compositions of the same volumetric size splashed significantly more water from the toilet bowl, compared to the cone 10 with a 35 degree point or less for an apex 13, when dropped therein. Prior art compositions, shapes, and methods of use do not anticipate or suggest using such a novel shaped novel composition in a toilet as a scenting agent after use of that toilet bowl by a woman for menstrual hygiene.

The novel cone 10 uses a pre-glass agglomeration powder that acts as a vector for a fragrance delivery by utilizing fused microspheres with calcium integrated into the spheres from an aqueous solution precursor. The fragrance delivery system is an artificial rock fragrance delivery system because the pre-glass agglomeration resembles a rock or rock-like structure. The novel cone 10 uses a powder derived from dust created during manufacture or ground from the rock-like structure to quickly release fragrance therein as well as oily fragrance dried around or into the powder particles. This powder is preferably dust made of an agglomeration of fused microspheres, and is more fully described in U.S. Pat. No. 6,769,271 issued to Mossbaugh on Aug. 3, 2004, which is incorporated herein by reference.

There is shown in FIG. 3 a cross-section of the cone 10 with the plenum 12, open and cone shaped, congruently located within the cone 10 to substantially increase the surface area exposed to water when the cone 10 is immersed in the toilet bowl water thereby increasing the effervescing action and fragrance delivery per unit of time.

Shown in FIG. 4 is another embodiment of the novel invention wherein the projectile shaped composite is shaped into a solid right circular cone 20 which is used by dropping into the water of a toilet bowl.

Preferably the invention uses a unique combination of effervescing material and the highly absorbent Mossbaugh pre-glass agglomeration by creating a powder from the agglomeration to create a short-term fragrance holding and release system for an aromatic liquid. This provides the secondary fragrance vector. Fragrance from the citric acid provides the first or primary fragrance vector.

The novel invention will be readily understood from the following description of an example.

EXAMPLE

Premix A $SiO_2$ from about 60% to about 75%;
$Na_2O$ from about 10% to about 35%;
$K_2O$ from about 2% to about 20%;
$B_2O_3$ from about 5% to about 20%; and
CaO from about 0.5% to about 12%

Preferably, commercial silicates are utilized such as sodium silicate having a weight ratio 3.22, or sodium silicate modified with a caustic agent or acetate having a weight range between 2.8-3 silicate to alkali, or potassium silicates such as KASIL (PQ Corporation) having a weight ratio 2.44 are used. Modifiers such as tech grade boric acid and calcium nitrate are also used. The slurry for the modifiers are approximately 8-18% solids. The total solution is between 20-40% solids.

A preferred method of making the pre-glass agglomeration of the Example comprises the following steps: The constituents are mixed together in two separate factions comprising the silicate part and the modifier part. The modifier part is boric acid and calcium in an aqueous slurry. The modifier solution is either poured into the silicate solution with vigorous mixing or the two are mixed together using an impeller pump with a recirculation loop. Vigorous mixing and slow addition of the boric/calcium solution is essential.

The solution, once mixed together, has a pH of 10-12. Mixing temperatures approach 60° C. This solution is fed to a two fluid nozzle for atomization via a diaphragm pump at 25-200 psi. Alternatively, a centrifugal atomizer may be utilized at 10,000-25,000 rpm. While air atomizing, air pressure varies between 80-1000 psi. The drying step occurs at about 100° C. to about 300° C. The outlet temperature is 300-800° F.

The spray-dried product is then fed via pneumatic conveyor to a rotary tube furnace. The powder is fed into the furnace via an Accurate Feeder to a 316 SS tube rotating at 7-12 rpm and an angle of repose approximately ⅛ to 5 inches per foot. The furnace is a standard thermal profile machine with at least 4 discrete zones set with a temperature profile from about 200° C. to about 1200° C. with either a co-current or a counter current dry air flow at approximately 25-200 SCFH. Another atmosphere that is reducing, methane for example, may be used.

The pre-glass agglomeration is then collected from the furnace and sifted with a 200 mesh screen, for example, to retrieve free flowing powder from the sintered pre-glass agglomeration. The sifted powder forms a mass of powder. Alternatively, fragments of the pre-glass agglomeration are gathered and ground into a powder. The pre-glass agglomeration powder, once formed, is dipped into a solution containing various fragrance(s) or essential oils and allowed to soak for a time period, e.g. approximately 20-30 minutes. Conversely, the pre-glass agglomeration can be placed in a shallow dish of oils and inserted into a high pressure oven at ambient temperatures to reduce absorption time. The pre-glass agglomeration powder is removed from the dip via a second screening process and conveyed under a series of dryers, for example ultraviolet heat lamps, in order to dry the pre-glass agglomeration powder to the touch.

Oils used in the absorption process are preferably cut with a carrier such as dipropylene glycol, propylene glycol, SD alcohols, etc.

Pre-Mix B

An amount of 1 Kg of sodium bicarbonate and 1 Kg of the pre-glass agglomeration powder pre-mixed with fragrance oils is placed into a mixing container, and is then mixed in the mixing container with approximately 60 g of water for a period of approximately four minutes. This causes the sodium bicarbonate to become moistened and allows subsequent absorption of a citric acid mixture.

After mixing this first mixture for a period of four minutes, 300 g of citric acid mixture is added. The citric acid mixture is formulated from 18 g of sodium borate, 180 g of citric acid powder and 213 g of citric acid granules. This citric acid mixture is mixed, for a period of approximately four seconds, into the first mixture in the mixing container and, when all the citric acid mixture has been added to the bowl, the mixing is maintained for a further period of about 40 seconds, depending on the humidity of the surrounding air.

The resulting third mixture is then packed into novel cone shaped tablet molds using enough pressure to form the required cone tablet shapes shown in FIG. 1 or FIG. 4. Once the shapes have been formed in the molds, and partially dried, the tablets are released from the molds and are then further dried by evaporation or by heating. By this process, there is produced an initial mild chemical reaction by which the sodium bicarbonate and the citric acid bind together chemically.

The tablets are dried naturally by evaporation over a period of 4 to 8 hours or, by the application of a combination of air flow and heat, over a shorter period, so that the chemical reaction is terminated within about 10 to 15 minutes. The resulting molded composition of matter is a new product with a new utility, namely, a scenting tablet for creation of a pleasant scent immediately after use of a toilet by dropping the product in the toilet with no or reduced splashing. It is a product that is hard and durable and yet effervescently emits fragrance when dropped into a toilet.

The composition formed by the above method of manufacture is a water-activated, dissolving, scent-releasing tablet with no or significantly reduced splash when dropped into toilet bowl water. The product and method comprises the step of dropping a cone shaped tablet tip first in the toilet bowl. Thereafter, the solution in the bowl interacts with the tablet to effervescently release an immediate pleasurable scent to fill the restroom. The product is a single use tablet. The method of use includes the essential step of dropping one cone shaped tablet, tip first, in the toilet bowl. The tablet for deposit into the bowl is used to release an immediate pleasurable fragrance of choice that will last for a short period of time, for example, 30 minutes to 1 hour after use. This toilet bowl tablet is formulated and uniquely shaped in a cone with about a 35 degree apex 13 to avoid splashing and to quickly deliver a fragrance using an effervescing agent after its deposit into the water in a toilet bowl. Obviously the smaller volume restrooms or powder rooms will allow a greater concentration of the fragrance from the tablet in the vicinity of the toilet.

The toilet fragrancing tablet of the present invention is a generally homogenous solid comprising at least two active fragrance-releasing agents and a bubbling aid such as an effervescing agent. The primary fragrance releasing agent releases the fragrance when the tablet is in first contact with water. The effervescing agent enhances the release of fragrance to the ambient air above the toilet bowl by creating a bubbling action and an admixing action. Any such agents known heretofore can be used and it is preferred that such agents are similar to that described in U.S. Pat. No. 5,997,901 incorporated herein by reference. In the present invention, an evaporatively released scent from a scent loaded pre-glass agglomeration comprises the secondary fragrance source.

According to the present invention, a method of manufacturing scented tablets comprises the steps of mixing sodium bicarbonate, water and a highly absorbent pre-glass agglomeration powder loaded with fragrance oils to form a first mixture, mixing sodium borate and citric acid to form a citric acid mixture, mixing together the first mixture and the citric acid mixture to form a third mixture, molding the third mixture to form right conical shaped tablets and drying the tablets to a hardened condition, e.g. by evaporation or by the application of heat and pressure. An initial mild chemical reaction causes the sodium bicarbonate and the citric acid to bind together chemically, trapping the pre-glass agglomeration powder particles loaded with fragrance therein.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by persons skilled in this art without departing from the scope of the present invention as defined by the following claims.

What is claimed is:

1. A cone shaped tablet comprising a composition of matter for emitting a fragrance upon immersion in water contained in a toilet bowl, the composition of matter comprising citric acid, the tablet further comprising a pre-glass agglomeration fragrance delivery system and sodium bicarbonate compacted together, the cone shaped tablet having a tip, the cone shaped tablet further comprising a splash reduction means for substantially reducing splashing of the water contained in the toilet bowl, the tablet being droppable into the water tip downward, said cone shaped tablet having a center of gravity therein, the cone shaped tablet further comprising a center of gravity shifting means for shifting the center of gravity of the cone shaped tablet toward said tip, said center of gravity shifting means for shifting the center-of-gravity of said cone shaped tablet toward said tip being a surface area increasing means for increasing the exposed surface area of said cone shaped tablet, said surface area increasing means is an aperture in the base of said cone shaped tablet, said aperture being the base of a right circular cone shaped plenum located within the tablet.

2. The cone shaped tablet of claim 1 wherein the pre-glass agglomeration fragrance delivery system is comprised of at least one fragrance oil.

3. The cone shaped tablet of claim 1 wherein the composition of matter is further comprised of water.

4. The cone shaped tablet of claim 1 wherein the composition of matter is further comprised of sodium borate.

5. A method for quietly and reduced-splashingly scenting ambient air near a toilet bowl comprising the steps of first providing a cone shaped tablet in accordance with claim 1 and then the step of dropping the tablet tip first into the water in the toilet bowl.

* * * * *